United States Patent [19]
Kwun et al.

[11] Patent Number: 6,000,288
[45] Date of Patent: Dec. 14, 1999

[54] DETERMINING AVERAGE WALL THICKNESS AND WALL-THICKNESS VARIATION OF A LIQUID-CARRYING PIPE

[75] Inventors: Hegeon Kwun; Keith A. Bartels, both of San Antonio, Tex.

[73] Assignee: Southwest Research Institute, San Antonio, Tex.

[21] Appl. No.: 09/063,362

[22] Filed: Apr. 21, 1998

[51] Int. Cl.[6] .................................................. G01N 29/04
[52] U.S. Cl. .............................. 73/597; 73/602; 73/643
[58] Field of Search ............................ 73/597, 598, 602, 73/622, 638, 643, 592; 702/39

[56] References Cited

U.S. PATENT DOCUMENTS

| | | | |
|---|---|---|---|
| 4,049,954 | 9/1977 | Da Costa Vieira et al. | 73/622 |
| 5,035,143 | 7/1991 | Latimer et al. | 73/597 |
| 5,456,113 | 10/1995 | Kwun et al. | 73/587 |
| 5,457,994 | 10/1995 | Kwun et al. | 73/587 |
| 5,581,037 | 12/1996 | Kwun et al. | 73/623 |

OTHER PUBLICATIONS

"Experimental observation of elastic–wave dispersion in bounded solids of various configurations," H. Kwun et al., *J. Acoust. Soc. Am.*, 99(2):962–968, Feb. 1996.

"Detection of corrosion in pipe using the magnetostrictive sensor technique," H. Kwun et al., in "Nondestructive Evaluation of Aging Maritime Applications," *SPIE–The International Society for Optical Engineering.*, vol. 2459, pp. 140–148, Jun. 8, 1995.

"Magnetostrictive Sensor Technology and Its Application," H Kwun et al., presented at Ultrasonics 1997, Delft, Netherlands, Jul. 1–4, 1997, pp. 1–17.

*Primary Examiner*—John E. Chapman
*Attorney, Agent, or Firm*—Venable; Robert Kinberg; Michael A. Sartori

[57] ABSTRACT

The average wall thickness and the wall-thickness variation of a liquid-carrying pipe are determined. An elastic wave is generated and is measured after traveling a distance along the pipe. From the received wave, the average radius of the pipe, the average inside diameter of the pipe, and the inside diameter variation of the pipe are determined. From the average radius of the pipe and the average inside diameter of the pipe, the average wall thickness of the pipe is determined. From the variations in the average radius of the pipe and the inside diameter variation of the pipe, the wall-thickness variation of the pipe is determined. To determine the average inside diameter of the pipe, the invention relies upon the coupling between the elastic wave modes propagating in the wall of the pipe and the modes propagating in the liquid within the pipe.

20 Claims, 5 Drawing Sheets

DETERMINING AVERAGE WALL THICKNESS AND WALL-THICKNESS VARIATION OF A LIQUID-CARRYING PIPE

FIELD OF THE INVENTION

The present invention relates to determining the average wall thickness and the variation in the wall thickness of a liquid-carrying pipe.

BACKGROUND OF THE INVENTION

The wall thickness of a pipe or tube used in plant equipment deteriorates over time. The wall thickness remaining in the pipe is an important parameter in evaluating the equipment's suitability for service. Currently, the remaining wall thickness of a pipe is determined by sampling the wall thickness at selected positions along the pipe using ultrasonic thickness gauges. Because the reliability of this sampling approach depends greatly on the statistical validity of the samples, the results of such an evaluation are subject to considerable uncertainty. This is particularly true when the number of samples is small because of the high cost of acquiring data. For example, data acquisition becomes expensive when there is too much surface area to cover. Further, the number of samples can be small because of limited accessibility to the pipe, such as when the pipe is under insulation or bundled together with other pipes.

SUMMARY OF THE INVENTION

It is an object of the present invention to provide a reliable and cost-effective approach to determining the average wall thickness and the wall-thickness variation of a liquid-carrying pipe.

Another object of the present invention is to determine the average wall thickness and the wall-thickness variation of a liquid-carrying pipe without removing insulation from the exterior of the pipe, without unbundling the pipe, without removing the liquid from the pipe, and without opening up the pipe.

The inventors have discovered that when a pipe is filled with liquid, coupling occurs between the longitudinal wave modes of the pipe and the wave modes in the water. When an elastic wave is propagated along a liquid-carrying pipe, the second longitudinal wave mode (L2) of the pipe is altered such that notches are produced in the frequency spectrum of the L2 mode, where a notch indicates a region where the spectral content is missing. Moreover, in some circumstances, when an elastic wave is propagated along a liquid-carrying pipe, a periodic series of signals that are separated by a regular time interval arises in the liquid-carrying pipe.

Using these physical phenomena discovered by the inventors, the inventors have further discovered that the average wall thickness and the wall-thickness variation of a liquid-carrying pipe can be determined. In particular, for the notch phenomenon, the average inside diameter of the pipe is inversely proportional to the frequencies at which the notches occur, and the inside diameter variation is related to the spread of these notch frequencies. For the periodic series of signals occurring at a regular time interval, the average inside diameter of the pipe is proportional to the time interval, and the inside diameter variation is related to the shape and duration of these signals. Using the average inside diameter and the inside diameter variation of the pipe, the average wall thickness and the wall-thickness variation can be determined.

The present invention includes a method, an apparatus, and an article of manufacture for determining the average wall-thickness and the wall-thickness variation of a liquid-carrying pipe. The method comprises: transmitting an elastic wave from a first point on the pipe; detecting a signal generated by the elastic wave traveling along the pipe; determining an average radius of the pipe from the detected signal; determining an average inside diameter of the pipe from the detected signal; determining the average wall thickness of the pipe from the average radius and the average inside diameter of the pipe; and determining variation of the wall thickness from the detected signal.

Further, the present invention includes an apparatus for implementing the method of the present invention. The apparatus includes a computer programmed with code segments to operate the computer in accordance with the present invention. Non-limiting examples of "computer" include: a general purpose computer; and any apparatus comprising a processing unit, memory, the capability to receive input, and the capability to generate output.

Moreover, the present invention includes an article of manufacture for implementing the method of the present invention on a computer. In particular, the article of manufacture of the present invention comprises a computer-readable medium embodying a computer program. For the present invention, the computer-readable medium embodying the computer program comprises code segments to control a computer to perform the method of the present invention.

Non-limiting examples of a "computer-readable medium" include: a magnetic hard disk; a floppy disk; an optical disk, such as a CD-ROM or one using the DVD standard; a magnetic tape; a memory chip; a carrier wave used to carry computer-readable electronic data, such as those used in transmitting and receiving electronic mail or in accessing a network, such as the Internet or a local area network ("LAN"); and any storage device used for storing data accessible by a computer.

Further, non-limiting examples of "code segments" include software, instructions, computer programs, or any means for controlling a computer.

The above objects and advantages of the present invention are illustrative, and not exhaustive, of thos e which can be achieved by the present invention. Thus, these and other objects and advantages of the present invention will be apparent from the description herein or can be learned from practicing the invention, both as embodied herein and as modified in view of any variations which may be apparent to those skilled in the art.

BRIEF DESCRIPTION OF THE DRAWINGS

The invention will be described in greater detail below by way of reference to the accompanying drawings, wherein similar reference characters refer to similar reference parts throughout the drawings, and wherein.

DETAILED DESCRIPTION OF THE PREFERRED EMBODIMENTS

Referring now to the accompanying drawings, the procedure of the present invention is depicted for a method, an apparatus, and an article of manufacture for determining the average wall thickness and the wall-thickness variation between two locations along a liquid-carrying pipe. The present invention relies on the dispersion characteristics of elastic wave modes (which are also called "guided wave modes") propagating in the pipe wall and the coupling of these modes with the modes propagating in the liquid in the pipe. Examples of liquids usable with the present invention include water, oil, and chemical acids. If the pipe is not carrying a liquid, the pipe will need to be filled with a liquid to use the present invention.

Figure 1:
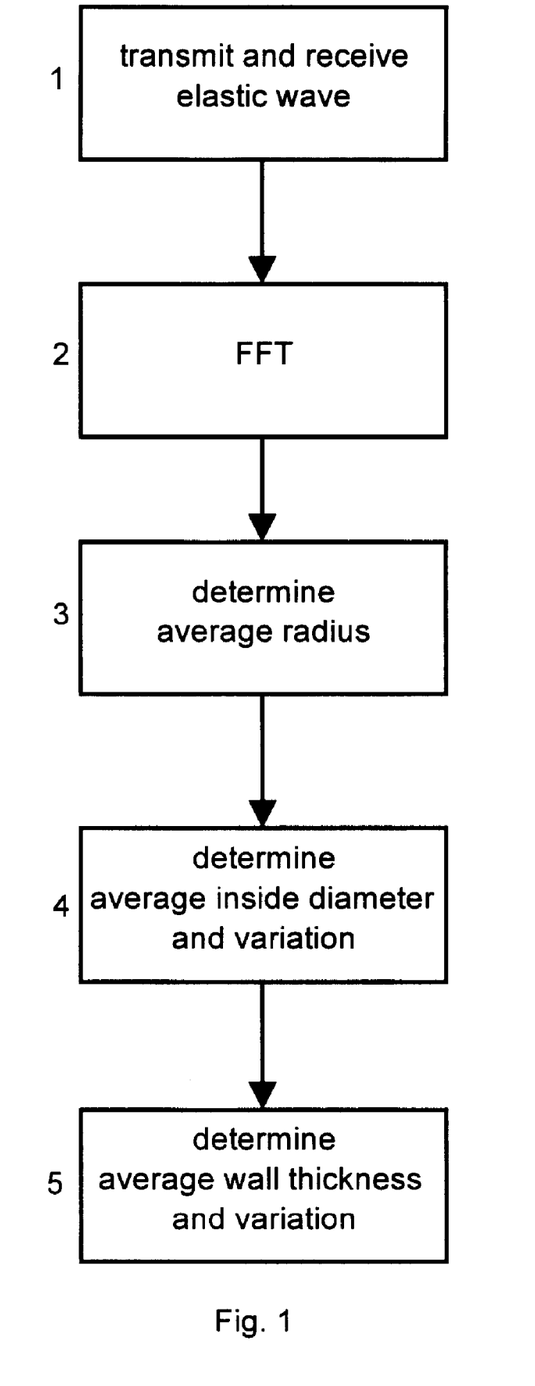
FIG. 1 illustrates the procedure of the present invention for determining the average wall thickness and the wall-thickness variation of a liquid-carrying pipe.

In block 1 of FIG. 1, an elastic wave is transmitted from a first point on the pipe. The elastic wave travels along the pipe and a signal representing the traveling elastic wave is detected. This is further illustrated in FIG. 2.

Figure 2:
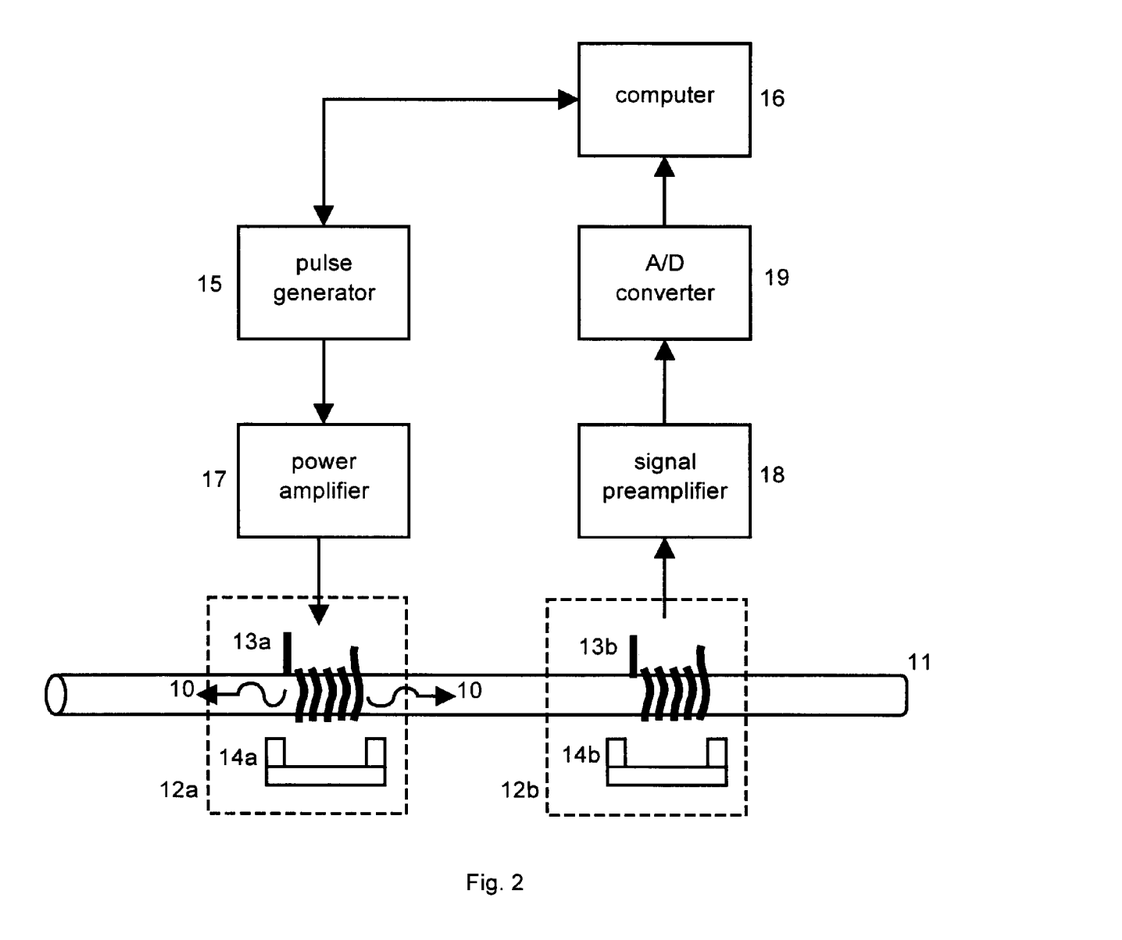
FIG. 2 is a schematic diagram of the instrumentation for the present invention.

In FIG. 2, the generated elastic wave 10 travels along the pipe 11. A first magnetostrictive sensor 12a is used to generate the elastic wave 10, and a second magnetostrictive sensor 12b is used to receive the elastic wave 10. Each magnetostrictive sensor 12a and 12b has a coil 13a and 13b and a bias magnetic 14a and 14b, respectively. Preferably, the magnetostrictive sensor described in U.S. Pat. Nos. 5,456,113, 5,457,994, and 5,581,037, which are incorporated herein by reference, is used.

To generate the elastic wave 10, a pulse generator 15, preferably under the control of a computer 16, generates a pulse. The pulse is amplified by a power amplifier 17, which is coupled to the pipe using the magnetoslrictive sensor 12a. The elastic wave 10 generated thereby is measured by the magnetostrictive sensor 12b, whose signal is transmitted to a signal preamplifier 18. The amplified signals from the signal preamplifier 18 is transmitted to the A/D converter 19. Preferably, the A/D converter 19 has at least an approximately one MHz sampling rate. The sampled signal from the A/D converter 19 is transmitted to the computer 16 as a time series signal for further processing.

Figure 4A:
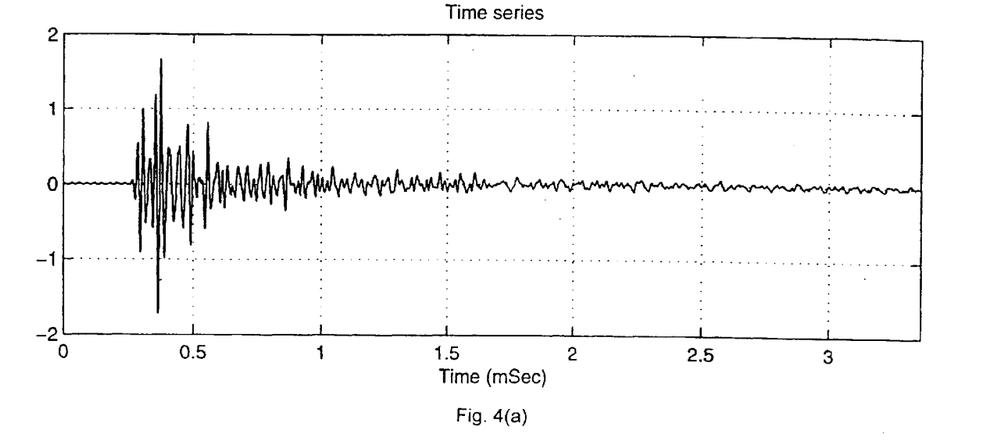
FIG. 4(a) illustrates the time series signal obtained from a water-filled pipe having a 4.5-inch outside diameter.

As an example, FIG. 4(a) depicts the time series signal produced by the A/D converter 19 and transmitted to the computer 16 for a water-carrying pipe having a 4.5-inch outside diameter and a 0.337-inch wall. The two magnetostrictive sensors 12a and 12b are separated by approximately 36 feet.

A further discussion of the instrumentation of the present invention can be found in the following publications, which are incorporated herein by reference: H. Kwun and K. A. Bartels, "Experimental Observation of Elastic-Wave Dispersion in Bounded Solids of Various Configurations," *Journal of the Acoustical Society of America*, 99(2):962–968, Feb. 1996; H. Kwun and K. A. Bartels, "Magnetostrictive Sensor Technologies and its Applications," presented at the 1997 Ultrasonics Conference in Delft, Netherlands, July 1–4, 1997; and H. Kwun, J. J. Hanley, and A. E. Holt, "Detection of Corrosion in Pipe Using the Magnetostrictive Sensor Technique," *Nondestructive Evaluation of Aging Maritime Applications* (R. B. Mignogna, Editor), SPIE, Vol. 2459, June 8, 1995, pp. 140–148.

Figure 3:
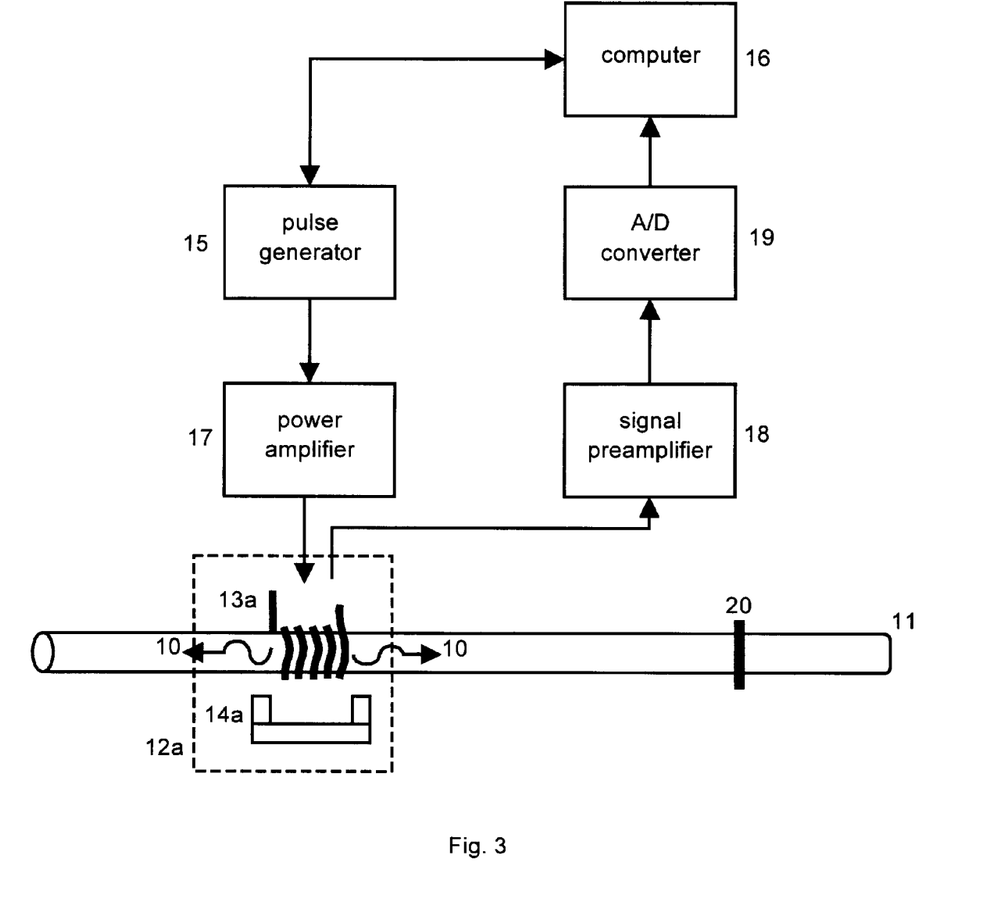
FIG. 3 is another schematic diagram of the instrumentation for the present invention.

As depicted in FIG. 2, the transmitting coil 13a generates the wave 10, and the receiving coil 13b receives the generated wave 10 after the wave 10 has traveled a distance along the pipe. Alternatively, instead of using two coils 13a and 13b as depicted in FIG. 2, a single coil 13a can be used, which is depicted in FIG. 3. For this case, the wave 10 generated by the transmitting coil 13a is reflected from a geometric reflector 20 of the pipe 11. Examples of such geometric reflectors include: flanges, tees, or welds. The wave 10 is reflected off the geometric reflector back to the transmitting coil 13a, which then acts as a receiving coil coupling the received signal to the signal preamplifier 18.

Figure 5:
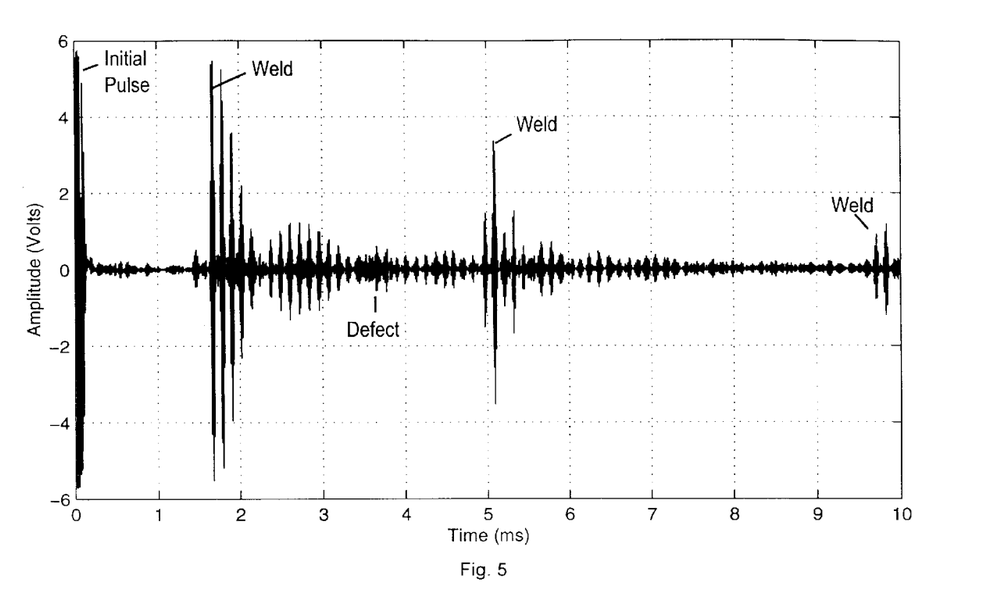
FIG. 5 illustrates the time series signal obtained from a diesel-filled pipe having a 6.625-inch outside diameter.

As an example, FIG. 5 depicts the time series signal produced by the A/D converter 19 and transmitted to the computer 16 for a diesel-carrying seamless carbon steel pipe having a 6.625-inch outside diameter and a 0.28-inch wall. The time series signal includes reflections from corrosion defects and from girth welds located approximately 4.37, 13.21, and 25.55 meters from the magnetostrictive sensor 12a.

Figure 4B:
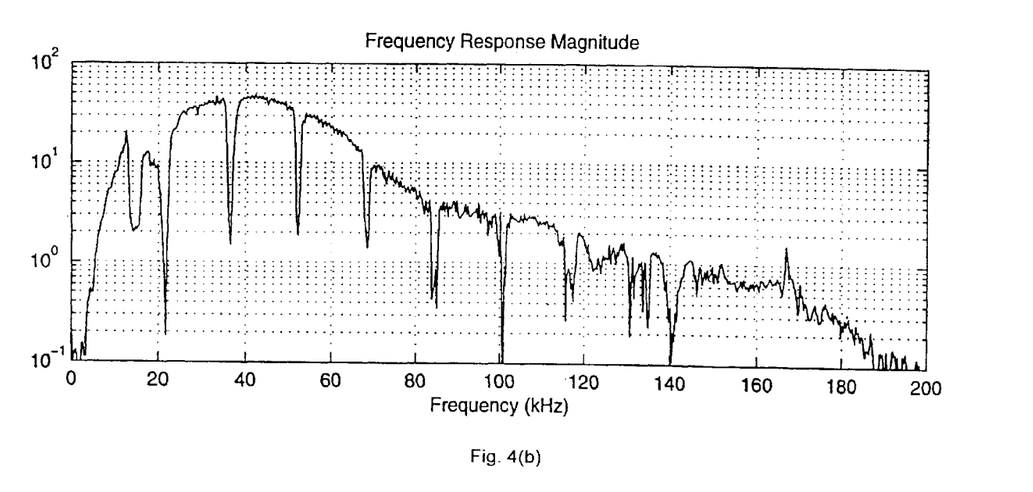
FIG. 4(b) illustrates the frequency domain signal for the time series signal of FIG. 4 (a).

In FIG. 1 in block 2, the time series signal received by the computer 16 from the A/D converter 19 is converted to a frequency domain signal. Preferably, this conversion is accomplished using the fast Fourier transform. As an example, FIG. 4(b) illustrates the magnitude of the frequency domain representation of the time series signal of FIG. 4(a) as determined via a discrete Fourier transform.

In block 3, the average radius of the pipe is determined from the frequency domain signal determined in block 2. In the frequency domain signal, a first notch frequency occurs between the first longitudinal mode L1 and the second longitudinal mode L2. Independent of whether there is liquid in the pipe, this notch occurs between L1 and L2, and is a characteristic property of wave propagation in a pipe. The frequency at which the above notch occurs, $f_{n0}$ is inversely proportional to the average radius of the pipe b, which is defined as (OD+ID)/4, where OD is the outside diameter and ID is the inside diameter of the pipe. In particular, the notch frequency $f_{n0}$ and the average radius b are related as follows:

$$f_{n0} = v_0/2\pi b \tag{1}$$

where $v_0$ is the rod velocity in the material of the pipe.

By measuring the notch frequency which separates the L1 and L2 modes, the average radius of the pipe b can be determined. As an example, in FIG. 4(b), the L1 mode occurs at approximately 12 kHz, and the L2 mode occurs at approximately 18 kHz. Using a peak picking routine on the frequency domain signal, the first notch occurs at approximately 15 kHz. Using equation (1) and $v_0 = 1.98 \times 10^5$ in/sec, the average radius b of the pipe is 2.101 inches.

In block 4, the average inside diameter of the pipe is determined from the frequency domain signal determined in block 2. In particular, the notch frequencies in the frequency domain signal occurring at frequencies greater than the first notch frequency are determined. As the inventors have discovered, these notch frequencies are caused by the liquid in the pipe.

In particular, the notches in the frequency domain beyond the L2 mode are produced by the mode coupling between the L2 mode in the pipe and the longitudinal wave modes in the liquid. The mode couplings between the pipe and the liquid occur at frequencies where the phase velocities of the wave modes in the pipe and the phase velocities of the wave modes in the liquid coincide. It should be noted that this phenomenon exists only when the pipe is filled with a liquid.

The inventors have further discovered that each of the notch frequencies in the frequency domain signal is proportional to the inverse of the inside diameter of the pipe. The relationship between the frequency $f_{ni}$ of notch i and the inside diameter of the pipe $ID_i$ is approximately:

$$ID_i = K v_L j_{li} / \pi f_{ni} \quad (2)$$

where i is an integer, K is a constant (whose value is approximately 1.06 in water), $v_L$ is the compressional wave velocity in the liquid, and $j_{li}$ is a root of the Bessel function $J_l(x)=0$. The first several values for $j_{li}$ are 3.8317, 7.0156, 10.1735, 13.3237, 16.4706, 19.6159, etc., for i=1, 2, 3, 4, 5, 6, etc.

Further, by averaging together the inside diameters determined for each notch frequency, the average inside diameter ID can be determined:

$$ID = \sum_{i=2}^{N} ID_i / N - 1 \quad (3)$$

where i=1 is excluded from the summation because the relationship in equation (2) is generally not as accurate when compared to i>1. By using equation (3) instead of equation (2), the accuracy in determining the average inside diameter of the pipe is increased.

As an example, consider the frequency domain signal illustrated in FIG. 4(b). The notch frequencies caused by the liquid are approximately 22 kHz, 36 kHz, 52 kHz, 68.5 kHz, 85 kHz, 101 kHz, etc. Using equation (2) and $V_L$=0.584–10$_5$ in/sec in water, the inside diameters computed using these six notch frequencies are 3.432, 3.840, 3.855, 3.833, 3.818, and 3.827 inches for i=1 to 6, respectively. Using equation (3), the average inside diameter is determined to be 3.835 inches.

Further, the relationship between the notch frequencies, the spread of the notch frequencies, the average inside diameter of the pipe, and the inside diameter variation of the pipe can be determined experimentally.

By using the present invention to obtain the notch frequencies, the spread of the notch frequencies, the inside diameter, and the inside diameter variation of various pipes, a lookup table can be generated. The rows of the lookup table correspond to notch frequencies, and the columns of the lookup table correspond to the spread of each notch frequency. Each entry in the lookup table contains the average inside diameter of the pipe and the inside diameter variation of the pipe.

Instead of one lookup table, two lookup tables can be developed. The first lookup table relates the notch frequencies to the average inside diameter of the pipe, and the second lookup table relates the spread of the notch frequencies to the inside diameter variation of the pipe. For any lookup table developed, interpolation can be used to provide for values that are not previously determined experimentally.

Instead of determining the average inside diameter and the inside diameter variation of the liquid-carrying pipe using the notch frequencies, these parameters of the liquid-carrying pipe can be determined from the time series signal. In particular, the inventors have discovered a phenomenon in the time series signal that occurs based on the liquid in the pipe and the duration of the signal transmitted into the pipe wall. The phenomenon is a periodic series of signals separated by a fixed time interval. The inventors have discovered that the time interval between the adjacent signals in the periodic series is proportional to the time required for a sound wave to travel diametrically through the liquid in the pipe.

With these discoveries, the average inside diameter ID of the pipe can be determined by measuring the time interval $t_r$ between adjacent signals of the periodic series phenomenon in the time series signal, and by multiplying the time interval $t_r$ by the compressional velocity of sound $v_L$ in the liquid:

$$ID = K t_r * v_L \quad (4)$$

where K is the proportionally constant used in equation (2). By measuring the time interval and knowing the compressional velocity of sound in the liquid, the average inside diameter of the pipe can be determined using equation (4).

Figure 6:
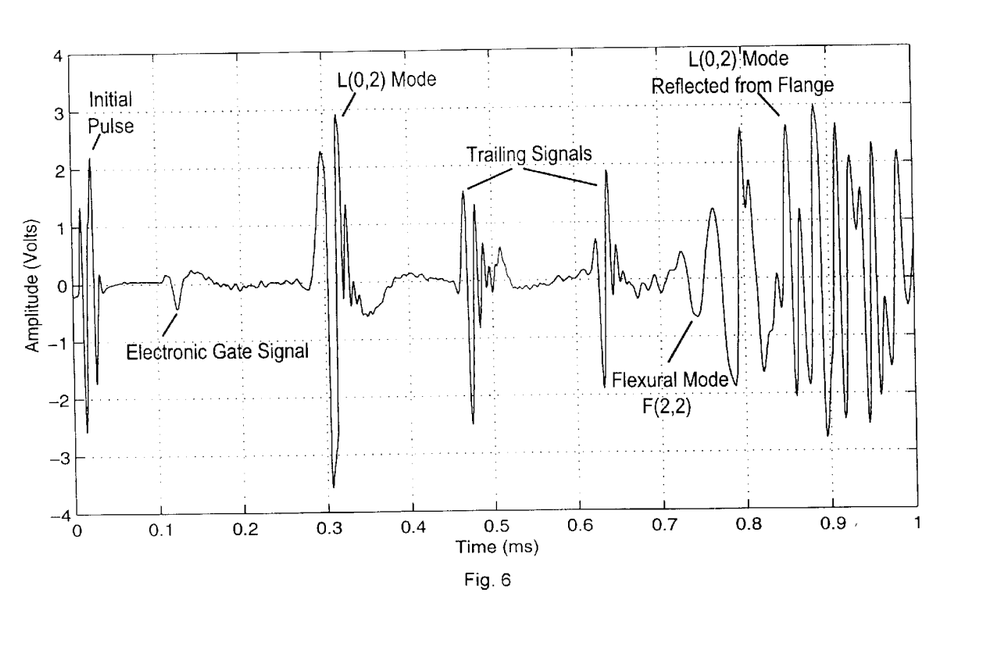
FIG. 6 illustrates the time series signal obtained from a water-filled pipe having a 10.75-inch outside diameter.

As an example, FIG. 6 depicts a time series signal having the periodic series phenomenon as output by the A/D converter 19. The time series signal was produced using a fresh water-carrying pipe having a 10.75-inch outside diameter and a 0.365-inch wall, and which was excited using the technique of the invention illustrated in FIG. 2. The time interval $t_r$ is 0.163 msec between the first and second adjacent signals of the periodic series phenomenon in the time series signal. Using equation (4), the average inside diameter of the pipe is 10.09 inches.

Further, the inside diameter variation of the pipe can be determined using the time series signal. If the inside diameter of the pipe varies, the signal waveform in the time series signal will change in shape and duration due to the interference of signals arriving at slightly different times. By correlating the shape and duration of the time series signal, the variation of the inside diameter of the pipe can be determined.

In comparing the above two approaches, namely, the notch frequency approach and the time series approach, for determining the average inside diameter and the inside diameter variation of the pipe, the inventors have discovered that the physical phenomenon of the notch frequencies occurs in all liquid-carrying pipes. Further, the inventors have discovered that the time series signal with the periodic series phenomenon occurs in pipes having an inside diameter which is larger than $Kv_L \Delta t$, where $\Delta t$ is the duration of the signal transmitted into the pipe wall. The presence of the periodic series phenomenon in the time series signal is therefore dependent upon the liquid in the pipe and the duration of the transmitted signal used. Hence, if the periodic series phenomenon occurs in the time series signal, equation (4) is preferably used; otherwise, the notch frequencies are determined and equation (3) is used.

In block 5 of FIG. 1, the average wall thickness and the wall-thickness variation are determined. The average radius b of the pipe, the average inside diameter ID of the pipe, and the outside diameter OD of the pipe are related as follows:

$$b = (ID + OD)/4 \quad (5)$$

Solving equation (5) for the outside diameter OD results in:

$$OD = 4b - ID \quad (6)$$

The average wall thickness h is related to the average inside diameter ID and the outside diameter OD as follows:

$$h = (OD/2) - (ID/2) \quad (7)$$

Substituting equation (6) into equation (7), the average wall thickness h can be determined from the average radius b and the average inside diameter ID as follows:

$$h = 2b - ID \tag{8}$$

The average radius b of the pipe is determined as discussed above for block 3, and the inside diameter ID of the pipe is determined as described above for block 4.

Further, the wall-thickness variation $v_h$ of the pipe can be determined as follows:

$$v_h = 2v_b - v_{ID} \tag{9}$$

where $v_b$ is the variation in the average radius b and $v_{ID}$ is the variation of the inside diameter. Hence, using the variations $v_b$ and $v_{ID}$, as determined above in block 4, the wall-thickness variation $v_h$ of the pipe can be determined.

For the measurements illustrated in FIGS. 4(a) and 4(b), the average radius b of the pipe is 2.101 inches, and the average inside diameter ID of the pipe is 3.835 inches. Using equation (8), the average wall thickness h of the pipe is 0.367 inches.

Further, the accuracy in determining the average wall thickness can be improved with the calibration of the parameters used in the equations, such as $v_o$, $V_L$, and K.

Blocks 2–5 of FIG. 1 are preferably implemented using code segments stored on a computer-readable medium and which are used to control the computer 16.

EXAMPLE

As an example, consider a water-carrying pipe with a 4.5-inch outside diameter and a 0.337-inch wall. Because the detected signals do not exhibit a periodic series of signals separated by a regular time interval, the first approach discussed in block 4 is used, wherein the average inside diameter is determined from the notch frequencies.

Consider the effect of a 10% loss in wall thickness due to erosion or corrosion. If the loss is entirely on the outside surface of the pipe, the average radius of the pipe is reduced from 2.082 inches to 2.065 inches, and the notch frequency at approximately 15 kHz, which separates the L1 and L2 modes, is increased by 0.8%, or 0.12 kHz.. Because only the outside surface of the pipe has changed, the inside surface of the pipe has not changed, and the notch frequencies are hence unchanged.

If the loss is entirely on the inside surface of the pipe, the average radius of the pipe is increased from 2.082 inches to 2.098 inches, and the notch frequency between the L1 and L2 modes is decreased by 0.8%, or 0.12 kHz. Since the inside diameter of the pipe is increased from 3.8:36 inches to 3.894 inches, the notch frequencies beyond the first notch frequency will decrease by approximately 1.78% percent. If a notch frequency occurs at 22 kHz, the change in frequency is 0.39 kHz, and if a notch frequency occurs at 101 kHz, the change in frequency is 1.8 kHz.

If the 10% loss to the wall thickness occurs equally to both the inside and outside surfaces, the average radius of the pipe is unchanged, and there is no change in the notch frequency between the L1 and L2 modes. However, the notch frequencies beyond the first notch frequency will be decreased by approximately 0.89%.

Instead of a 10% loss in wall thickness, consider the case of a 0.01-inch change in the average radius of the pipe. This produces an approximately 0.07 kHz change in the first notch frequency between the L1 and L2 modes. If the 0.01-inch change occurs entirely to the inside diameter of the pipe, the notch frequencies in the range from 20 to 100 kHz decrease by approximately 0.10 to 0.52 kHz. Thus, from the behavior of the changes in the notch frequencies and from the average wall thickness measurement, the manner in which the wall loss occurs can be determined.

The accuracy in the wall-thickness measurements depends directly on the accuracy and resolution of the frequency measurements. For this example, currently available A/D converters and timing devices for controlling the transmitting, receiving, and signal averaging are able to obtain a resolution of greater than 0.01 kHz.

The invention has been described in detail with respect to preferred embodiments, and it will now be apparent from the foregoing to those skilled in the art that changes and modifications may be made without departing from the invention in its broader aspects. Therefore, the invention, as defined in the appended claims, is intended to cover all such changes and modifications as fall within the true spirit of the invention.

What is claimed is:

1. A method for determining parameters of a liquid-carrying pipe, comprising:

transmitting an elastic wave from a first point on the pipe;

detecting a signal generated by the elastic wave traveling along the pipe;

determining an average radius of the pipe from the detected signal;

determining an average inside diameter of the pipe from the detected signal; and determining an average wall thickness of the pipe from the average radius and the average inside diameter of the pipe.

2. A method according to claim 1, further comprising:

converting the detected signal to a frequency domain signal; wherein determining the average radius of the pipe comprises:

detecting a notch frequency in the frequency domain signal between a first longitudinal mode (L1) and a second longitudinal mode (L2) of the frequency domain signal; and determining the average radius of the pipe from the notch frequency.

3. A method according to claim 1, further comprising:

converting the detected signal to a frequency domain signal; wherein determining the average inside diameter of the pipe comprises:

detecting notch frequencies in the frequency domain signal caused by liquid in the pipe; and determining the average inside diameter of the pipe from the notch frequencies.

4. A method according to claim 3, further comprising:

determining spread of the notch frequencies; and determining variation of the inside diameter of the pipe from the spread of the notch frequencies.

5. A method according tc claim 1, wherein the detected signal comprises a time series signal having a periodic series caused by liquid in the pipe, and wherein determining the average inside diameter of the pipe comprises:

determining a time interval between adjacent signals in the periodic series of the time series signal; and determining the average inside diameter from the time interval.

6. A method according to claim 5, further comprising:

determining variation of the inside diameter of the pipe from the changes in the time series signal.

7. A method according to claim 1, wherein determining the average wall thickness of the pipe comprises:

subtracting the average inside diameter of the pipe from twice the average radius of the pipe.

8. A method according to claim 1, wherein detecting the signal comprises:

detecting the signal at a second point separated by a predetermined distance along the pipe from the first point.

9. A method according to claim 1, wherein detecting the signal comprises:

detecting the signal at the first point.

10. A method according to claim 1, further comprising determining variation of the wall thickness of the pipe from the detected signal.

11. An apparatus for determining parameters of a liquid-carrying pipe, comprising:

means for transmitting and receiving an elastic wave along the pipe;

a converter for converting the received elastic wave to a detected signal; and a computer programmed with code segments comprising:

code segments for determining an average radius of the pipe from the detected signal;

code segments for determining an average inside diameter of the pipe from the detected signal; and code segments for determining an average wall thickness of the pipe from the average radius and the average inside diameter of the pipe.

12. An apparatus according to claim 11, the code segments further comprising:

code segments for converting the detected signal to a frequency domain signal;

wherein the code segments for determining the average inside diameter of the pipe comprise:

code segments for detecting notch frequencies in the frequency domain signal caused by liquid in the pipe; and code segments for determining the average inside diameter from the notch frequencies.

13. An apparatus according to claim 11, wherein the detected signal comprises a time series signal having a periodic series caused by liquid in the pipe, and wherein the code segments for determining the average inside diameter of the pipe comprise:

code segments for determining a time interval between adjacent signals in the periodic series of the time series signal; and code segments for determining the average inside diameter from the time interval.

14. An apparatus according to claim 11, wherein the code segments further comprises code segments for determining variation of the wall thickness of the pipe from the detected signal.

15. An apparatus according to claim 11, wherein the means for transmitting and receiving comprises:

a first magnetostrictive sensor; and a second magnetostrictive sensor separated by a predetermined distance from the first magnetostrictive sensor.

16. An apparatus according to claim 11, wherein the means for transmitting and receiving comprises a magnetostrictive sensor.

17. A computer-readable medium embodying code segments for determining parameters of a liquid-carrying pipe, comprising:

code segments for determining an average radius of the pipe from a detected signal representative of a signal generated by an elastic wave traveling along the pipe;

code segments for determining an average inside diameter of the pipe from the detected signal; and code segments for determining an average wall thickness of the pipe from the average radius and the average inside diameter of the pipe.

18. A computer-readable medium according to claim 17, further comprising:

code segments for converting the detected signal to a frequency domain signal;

wherein the code segments for determining the average inside diameter of the pipe comprise:

code segments for detecting notch frequencies in the frequency domain signal caused by liquid in the pipe; and code segments for determining the average inside diameter from the notch frequencies.

19. A computer-readable medium according to claim 17, wherein the detected signal comprises a time series signal having a periodic series caused by liquid in the pipe, and wherein the code segments for determining the average inside diameter of the pipe comprise:

code segments for determining a time interval between adjacent signals in the periodic series of the time series signal; and code segments for determining the average inside diameter from the time interval.

20. A computer-readable medium according to claim 17, further comprising code segments for determining variation of the wall thickness of the pipe from the detected signal.

* * * * *